United States Patent
Consoli et al.

(10) Patent No.: US 11,636,954 B2
(45) Date of Patent: Apr. 25, 2023

(54) SUBJECT CLUSTERING METHOD AND APPARATUS

(71) Applicant: KONINKLIJKE PHILIPS N.V., Eindhoven (NL)

(72) Inventors: Sergio Consoli, Nuenen (NL); Monique Hendriks, Eindhoven (NL); Pieter Christiaan Vos, Vught (NL); Jacek Lukasz Kustra, Eindhoven (NL); Ralf Dieter Hoffmann, Brueggen (NL); Dimitrios Mavroeidis, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 327 days.

(21) Appl. No.: 16/648,797

(22) PCT Filed: Sep. 18, 2018

(86) PCT No.: PCT/EP2018/075238
§ 371 (c)(1),
(2) Date: Mar. 19, 2020

(87) PCT Pub. No.: WO2019/057727
PCT Pub. Date: Mar. 28, 2019

(65) Prior Publication Data
US 2020/0219627 A1    Jul. 9, 2020

(30) Foreign Application Priority Data
Sep. 20, 2017    (EP) ..................... 17192198

(51) Int. Cl.
*G16H 50/70*    (2018.01)
*G16H 10/60*    (2018.01)
(Continued)

(52) U.S. Cl.
CPC .......... *G16H 50/70* (2018.01); *G06F 16/285* (2019.01); *G06N 20/00* (2019.01); *G16H 10/60* (2018.01); *G16H 50/20* (2018.01)

(58) Field of Classification Search
None
See application file for complete search history.

(56) References Cited

U.S. PATENT DOCUMENTS 6,952,700 B2    10/2005    Modha et al.
8,504,392 B2    8/2013    Saria et al.
(Continued)

FOREIGN PATENT DOCUMENTS

JP    2012150786 A    8/2012

OTHER PUBLICATIONS

International Search Report and Written Opinion for International Application No. PCT/EP2018/075238, filed Sep. 18, 2018, 17 pages.
(Continued)

*Primary Examiner* — Kevin Y Kim

(57) ABSTRACT

A method of clustering or grouping subjects that are similar to one another. A dataset contains, for each subject, a set of quantitative values which each represent a respective clinical or pathological feature of that subject. A principal component analysis, PCA, is performed on the dataset. Loadings of one of the first two principal components identified by the PCA are used to generate a respective dataset of weighting values. These weighting values are used to weigh or modify each set of quantitative values in the dataset. A clustering algorithm is performed on the weighted sets of subject data. The process may be iterated until user-defined stopping conditions are satisfied.

18 Claims, 8 Drawing Sheets

(51) Int. Cl.
*G16H 50/20* (2018.01)
*G06F 16/28* (2019.01)
*G06N 20/00* (2019.01)

(56) References Cited

U.S. PATENT DOCUMENTS

| | | |
|---|---|---|
| 8,918,396 B2 | 12/2014 | Nagano et al. |
| 2005/0209785 A1 | 9/2005 | Wells et al. |
| 2010/0177950 A1 | 7/2010 | Donovan et al. |
| 2012/0041779 A1 | 2/2012 | Boroczky |

OTHER PUBLICATIONS

Yeung, et al., "Improving performance of similarity-based clustering by feature weight learning", IEEE Transactions on Pattern Analysis in Machine Intelligence, vol. 24, Issue 4, Apr. 2002, 2 pages. (Abstract).
Dhillon I. S., et al., "Concept decompositions for large sparse text data using clustering", Machine Learning 42, 1/2 (2001): 143-175.
Gendreau M., et al., "Metaheuristics in Combinatorial Optimization." Annals of Operations Research 140, (2005): 189-213. (Abstract).
Modha D. S., et al., "Feature Weighling in k-Means Clustering." Journal of Machine Learning 52, 3 (2003):217-237.
Qian B., et al., "A relative similarity based method for interactive patient risk prediction". Data Mining and Knowledge Discovery 29,4 (2015):1070-1093. (Abstract).
Wang F., et al., "Composite distance metric integration by leveraging multiple experts' inputs and its application in patient similarity assessment", Statistical Analysis and Data Mining 5, 1 (2012):54-69. (Abstract).

SUBJECT CLUSTERING METHOD AND APPARATUS

RELATED APPLICATIONS

This application is the U.S. National Phase application under 35 U.S.C. § 371 of International Application No. PCT/EP2018/075238, filed on Sep. 18, 2018, which claims the benefit of and priority to European Application No. 17192198.4, Sep. 20, 2017. These applications are incorporated by reference herein.

FIELD OF THE INVENTION

This invention relates to the field of clustering subjects, and more specifically to the field of clustering using data of the subjects.

BACKGROUND OF THE INVENTION

Grouping of subjects is a regular activity in clinical practice with the aim of defining the best treatment options for a given subject. Specifically, if subjects can be accurately grouped together into similar groups, this would allow for a clinician to easily compare a given subject or case to similar subjects or cases to identify a potential diagnosis, suitable treatment options and likely outcomes of said treatment options. This tends to result in improved subject outcome and more accurate diagnosis, as relevant historical medical data (i.e. of similar cases) can be accurately identified and utilized by a clinician.

There is therefore an increasing desire to improve the accuracy of a grouping process. However, due to the typically large number of variables or possibly influential characteristics of a subject, it is difficult for even the experienced clinician to determine whether two subjects are similar or not. Clinicians have therefore turned to automated or unsupervised 'machine-learning' (ML) methods for grouping subjects.

Conventional grouping methods assume that all features (i.e. variables or characteristics) are statistically similar, for example, having a similar range or having similar variation ranges and statistical distributions. However, subject data (e.g. biomedical information) is usually heterogeneous, and different data therefore tends to belong in different domains with a high degree of statistically dissimilarity. This leads to significantly reduced accuracy when performing a conventional clustering method.

SUMMARY OF THE INVENTION

The invention is defined by the claims.

There is proposed a method of clustering similar subjects of a plurality of subjects, the method comprising: obtaining a dataset of subject data, the dataset containing a respective set of quantitative values for each subject, each quantitative value being a measurement of a clinical or pathological feature of the subject and each set of quantitative values having a same number of quantitative values; and performing a clustering process comprising: performing a principle component analysis on the dataset of subject data to identify at least two principle components, each principal component being associated with component scores and a dataset of loadings, the number of loadings in each dataset of loadings being equal to the number of quantitative values in the dataset of subject data; generating a first dataset of weighting values, each weighting value being based on a respective loading in the dataset of loadings associated with one of the first two principle components, the number of weighting values in the first dataset being equal to the number of loadings in the dataset of loadings; weighting the quantitative values of the dataset of subject data using the first dataset of weighting values to obtain a weighted dataset of subject data; and performing a clustering algorithm on the weighted dataset of subject data so as to cluster similar subjects into groups of subjects having similar clinical characteristics, wherein subjects in each group of subjects have a similar diagnosis, predicted subject outcome and/or suitable treatment options.

There is therefore proposed a method of modifying subject data according to statistical information of the subject data and performing a clustering process based on the modified subject data. In particular, a principle component analysis, PCA, is performed to generate a dataset of weighting values for modifying the subject data. The modification to the subject data allows subjects to be grouped into groups (of similar subjects) with a higher degree of accuracy and with an improved degree of separation between the groups.

In turn, this allows improved diagnosis capabilities, selection of appropriate treatment options and prediction of probable subject outcomes for a selected treatment option. Thus, overall subject outcome can be significantly improved.

The present invention recognizes that generating appropriate weighting values based on a principle component analysis allows for a statistical variation between different measurable features of a subject (i.e. a subjects characteristics or variables) to be reduced, such that the features become more statistically similar. This allows for improved accuracy when grouping similar subjects, as the influence of potentially statistically unbalanced features (e.g. features having an extremely large standard deviation or range) on a clustering method is reduced.

Principle component analysis has been herein recognized as a method of allowing more accurate and precise identification of suitable weighting values that result in subject data which can be clustered into groups of greater similarity and improved separation. The loadings associated with of one the most influential principal components (being one of at least the first two principal components) are used as a basis for generating the weighting values and therefore as a basis for modifying the dataset of subject data.

The method may further comprise a step of obtaining a second dataset of weighting values, the number of weighting values in the second dataset being equal to the number of quantitative values in the dataset of subject data, and wherein the step of generating the first dataset of weighting values comprises modifying each weighting value in the second dataset of weighting values based on a respective loading in the dataset of loadings associated with one of the first two principle components, to thereby obtain the first dataset of weighting values.

Thus, the first dataset of weighting values may be calculated, generated or obtained by modifying an existing dataset of weighting values, which may be an initial dataset of weighting values or a result of a previous iteration of a weighting value generation step. This initial dataset or previous dataset is labelled the second dataset of weighting values.

There are therefore proposed embodiments which allow weighting values to be adjusted and altered. This allows for historical weighting values (e.g. weighting values previously used or generated in a previous weighting value generation step) to be used in subsequent clustering methods. This may reduce a workload of generating an appropriate dataset of weighting values, and enable iterative procedures to iteratively generate a converging set of appropriate weighting values.

In some embodiments, the modifying each weighting value in the second dataset of weighting values comprises: selecting a dataset of loadings associated with one of the first or second principal components; and multiplying each weighting value in the second dataset of weighting values by a respective loading in the dataset of loadings associated with the selected principal component, to obtain a modified, first dataset of weighting values.

In further embodiments, modifying each value in the second dataset of weighting values further comprises dividing each weighting value in the second dataset of weighting values by a randomly or pseudorandomly selected number between 0 and 1.

In this way, each weighting value of the second dataset of weighting values is modified as a random proportion of a respective loading in a dataset of loading values. This allows for a degree of randomness to be introduced into the modification of the subject data set, which allows for a fair diversification strategy to be implemented.

This may be particularly important in an iterative search (for suitable weighting values) in order to improve a likelihood of appropriate weighting values being identified. In particular, this allow a heuristic search to be performed to more accurately and efficiently generate a converged dataset of weighting values.

The modifying each value in the second dataset of weighting values may comprise modifying each value in the second dataset of weighting values based on a respective loading in the dataset of loadings associated with a randomly or pseudorandomly selected one of the first two principal components.

Thus, embodiments provide for further randomness in the generation of the first dataset of weighting values by a non-deterministic selection between the most influential principal components. This may further improve a likelihood and efficiency of an appropriate dataset of weighting values being calculated or identified (especially during an iterative procedure).

The performing of the clustering process optionally comprises iteratively performing the clustering process, wherein the clustering process (optionally) further comprises: calculating a quality value indicative of the quality of the clustering performed by the clustering algorithm; in response to the quality value being greater than a first predetermined threshold, replacing the weighting values in the second dataset of weighting values with the weighting values in the first dataset of weighting values; and in response to the quality value being below the first predetermined threshold, rejecting the first dataset of weighting values and retaining the weighting values of the second dataset of weighting values.

Embodiments of the invention therefore provide an iterative process of calculating the weighting values in order to generate a satisfactory or optimized dataset of weighting values which allows for the subject data to be modified to a high degree of accuracy, such that there is improved separation between groups of subjects and improved similarity of subjects within a group. This significantly improves a performance of an overall clustering method. The optimized dataset of weighting values is, after each iteration, represented by the second dataset of weighting values. In particular, after each iteration, the second dataset of weighting values represents the dataset of weighting values that improves the quality of the clustering process to the best of known capabilities.

An evaluation method for a generated dataset of weighting values may therefore be performed, to determine whether a newly generated dataset (first dataset) of weighting values has improved a quality of the subject data, such as a separation between groups of subjects. The evaluation method calculates a quality value indicative of the quality of the clustering. Any known quality value generation method may be used, as would be appreciated by the person skilled in the art.

The proposed method rejects adjustments, modifications or alterations to the weighting values which do not improve a quality of the clustering or do not otherwise ensure that a quality of the clustering is above a predetermined value. The predetermined value may, for example, be determined based on a quality value calculated during a previous iteration of the clustering process, or may be a standardized value (e.g. 0.5).

In at least one further embodiment, the method further comprises discontinuing performing the iterative clustering process in response to any one or more of: the quality value being greater than a second predetermined threshold; a number of iterations being greater than a predetermined iteration number; a length of time elapsed during the iterative clustering process being greater than a predetermined length of time; and a number of consecutive rejections of the first dataset of weighting values being greater than a predetermined number of rejections.

The method may therefore be adapted to only iteratively perform the clustering process for a certain number of times. The number of times that the iterative process is performed may be restricted based, for example, a predetermined number of iterations (e.g. 25 or 50 iterations), a predetermined time spent performing the iterative clustering process (e.g. 30 minutes or 1 hour). Preferably, the iterative process is stopped when a suitable or predefined level of similarity between groups of subjects has been attained and/or the iteration process converges. This may be respectively indicated by, for example, a quality value going above a predetermined value (e.g. an average silhouette width rising above 0.5) or a new dataset of weighting values being rejected for a predetermined number of iterations (e.g. 5 iterations).

The above embodiments may prevent an iteration process being performed for an excessive period of time (thereby reducing processing power) without significantly affecting the likelihood that an appropriate or optimized dataset of weighting values is calculated. An efficiency of the method is therefore improved and redundant calculations are avoided.

The first predetermined value may be a quality value of a clustering performed by the clustering algorithm based on the dataset of subject data weighted using the second dataset of weighting values. The second dataset of weighting values may represent the initial dataset of weighting values and/or a dataset of weighting values generated in a previous iteration.

Thus, the modified first dataset of weighting values may be rejected if the quality value for the clustering process is not improved in a subsequent iteration. This allows for a convergence of a suitable dataset of weighting values to be attained, by only permitting a newly generated dataset of weighting values to proceed to a subsequent iteration if that set of values improves a clustering of subjects.

In some embodiments, the method comprises, during the iterative clustering process and in response to the quality value being greater than a first predetermined threshold, replacing the first predetermined threshold with the quality value. Thus, the quality value may be set as a threshold value for a subsequent iteration.

Optionally, the method further comprises: weighting the quantitative values using the second dataset of weighting values to obtain an initial weighted dataset of subject data; performing a clustering algorithm on the initial weighted dataset of subject data so as to cluster similar subjects; and calculating a quality value indicative of the quality of the clustering performed by the clustering algorithm to thereby obtain the first predetermined threshold.

The calculating a quality value may comprise calculating one or more of: a Dunn index; a Silhouette width and a Davies-Bouldin index. Other quality values will be readily apparent to the skilled person.

Preferably the quality value indicates a degree of separation between different clusters or groups of subjects. However, any known quality value for a result of a clustering algorithm may be employed. For example, a quality value may indicate a similarity between subjects within any given group, which is also indicative of an improvement to the overall subject data.

A computer program product comprising a computer readable storage medium having computer readable program instructions embodied therewith to, when executed on a processor arrangement, cause said processor arrangement to implement any previously described method.

According to another aspect of the invention, there is provided a processor arrangement adapted to cluster similar subjects of a plurality of subjects, the processor arrangement comprising: an obtaining unit adapted to obtain a dataset of subject data, the dataset containing a respective set of quantitative values for each subject, each quantitative value being a measurement of a clinical or pathological feature of the subject and each set of quantitative values having a same number of quantitative values; and a clustering unit adapted to perform a clustering process by: performing a principal component analysis on the dataset of subject data to identify at least two principal components, each principal component being associated with a component score and a dataset of loadings, the number of loadings in each dataset of loadings being equal to the number of quantitative values in a set of quantitative values; generating a first dataset of weighting values, the number of weighting values in the first set being equal to the number of loadings in a dataset of loadings, wherein each weighting value in the first dataset of weighting values is based on a respective loading in the dataset of loadings associated with one of the first two principal components; weighting the quantitative values using the second dataset of weighting values to obtain a weighted dataset of subject data; and performing a clustering algorithm on the weighted dataset of subject data so as to cluster similar subjects into groups of subjects having similar clinical characteristics, wherein subjects in each group of subjects have a similar diagnosis, predicted subject outcome and/or suitable treatment options.

The processor arrangement may be adapted, wherein: the obtaining unit is adapted to obtain a second dataset of weighting values, the number of weighting values in the second set being equal to the number of quantitative values in a set of quantitative values, and the clustering unit is adapted to generate the first dataset of weighting values by modifying each weighting value in the second dataset of weighting values based on a respective loading in the dataset of loadings associated with one of the first two principal components, to thereby obtain the first dataset of weighting values.

The clustering unit may be adapted to iteratively perform the clustering process, and wherein the clustering process further comprises: calculating a quality value indicative of the quality of the clustering performed by the clustering algorithm; in response to the quality value being greater than a first predetermined threshold, replacing the weighting values in the second dataset of weighting values with the weighting values in the first dataset of weighting values; and in response to the quality value being below the first predetermined threshold, rejecting the first dataset of weighting values and retaining the weighting values of the second dataset of weighting values.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

According to a concept of the invention, there is proposed a method of clustering or grouping subjects that are similar to one another. A dataset contains, for each subject, a set of quantitative values which each represent a respective clinical or pathological feature of that subject. A principal component analysis, PCA, is performed on the dataset. Loadings of one of the first two principal components identified by the PCA are used to generate a respective dataset of weighting values. These weighting values are used to weigh or modify each set of quantitative values in the dataset. A clustering algorithm is performed on the weighted sets of subject data. The process may be iterated until user-defined stopping conditions are satisfied.

Embodiments are at least partly based on the realization that appropriate weighting of subject data may reduce statistical variation between different parameters or variables in that subject data, and thereby improve a clustering quality. In particular, it has been recognized that a principal component analysis allows those variables contributing the most significant statistical deviance in a dataset of subject data to be mitigated.

Illustrative embodiments may, for example, be employed in clinical environments to allow a clinician to more accurately and effectively group similar subjects into groups using an improved autonomous process. In particular, subjects are grouped based on similar clinical characteristics, i.e. subjects in a particular group may have a similar diagnosis, a similar predicted subject outcome and/or similar suitable treatment options (including e.g. similar predicted outcome of such treatment options). This will significantly improve a likelihood of accurately diagnosing a subject (e.g. as similar historic cases may be grouped together), improved prediction of subject outcome and improved selection of appropriate treatments, thereby leading to improvements to overall subject outcome.

Figure 1:
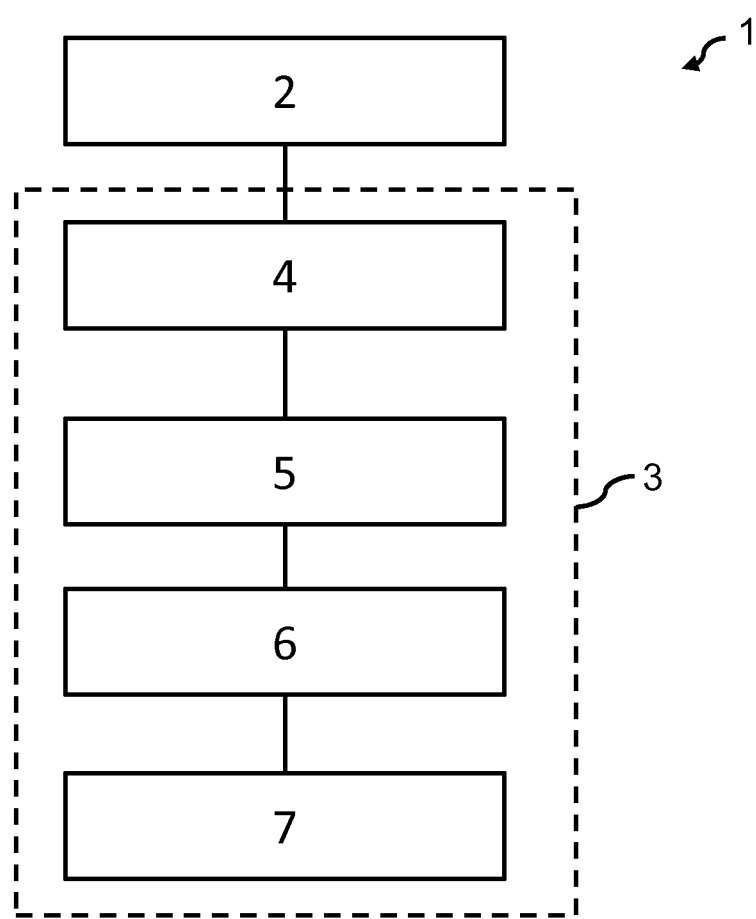
FIG. 1 illustrates a method of clustering subjects according to a first embodiment.

FIG. 1 illustrates a method 1 of clustering subjects according to an embodiment.

The method comprises a step 2 of obtaining a dataset of subject data and a clustering process 3 or routine.

The dataset obtained in step 2 contains, for each subject, a respective set of quantitative values. Each quantitative value represents a different (clinical or pathological) feature or characteristic of a subject, such that the subject may be associated with any plurality of variables (i.e. features or characteristics).

Conceptually, the dataset represents a plurality of records, each record being associated with a different subject. Each record contains a set of fields or variables, each field being associated with a respective quantitative value. Thus, each field of a record may represent a different pathological or clinically relevant parameter, variable or characteristic of a subject associated with the record.

A quantitative value may indicate, for example, the clinical stage of the subject, a percentage of positive biopsy scores, a pulse rate of the subject, an age of the subject, a number of hospital admissions of the subject, a primary and/or secondary biopsy Gleason score of the subject, a prostate-specific antigen density, and so on. Each set of quantitative values (i.e. each subject) has a same number of quantitative values contained therein. Missing quantitative values may be set to zero, a default value or an average value, as explained later. In the context of the present invention, a quantitative value may thereby be a numerical representation of a particular sign or symptom of a subject (e.g. temperature or pain score).

The clustering process 3 comprises a step 4 of performing a principal component analysis, PCA, on the dataset of subject data. A principal component analysis identifies at least two principal components of the subject data in accordance with known schemes. Each principal component is generally associated with component scores and a dataset of loadings for each component score.

The clustering process 3 also comprises a step 5 of generating a first dataset of weighting values. Each weighting value is based on a respective loading of a selected dataset of loadings. The number of weighting values is equal to the number of loadings (in a dataset of loadings) as well as the number of quantitative values in a set of quantitative values. The selected dataset of loadings is associated with one of the first two principal components, obtained during the principal component analysis step 4. The first two principal components are those two components that explain most of the variance in the dataset, as would be readily appreciated by the skilled person.

The clustering process 3 also comprises a step 6 of weighting each quantitative value in the dataset of subject data using the first dataset of weighting values. In particular, each quantitative value is weighted based on a respective loading in the first dataset of loadings. Thus, by way of example, the first quantitative value in a first set of quantitative values is weighted based on a first loading in the first dataset of loadings. Weighting each quantitative value in this way produces a weighted dataset of subject data.

The clustering process 3 also comprises a step 7 of performing a clustering algorithm on the weighted dataset of subject data. In other words, the dataset is modified by weighting values and subsequently clustered into groups of similar subjects. This clustering algorithm may be any known clustering algorithm, such as k-means clustering (being a centroid model), a hierarchical clustering analysis, a biclustering process and so on.

Performing the clustering process on subject data, which has been modified based on an outcome of a PCA process, results in improved clustering of subjects and improved separation between groups of subjects. As previously explained, this results in improved diagnosis capabilities, improved selection of appropriate treatment options and improved prediction of probable subject outcomes for a selected treatment option. In particular, historical data may be more accurately catalogued and compared (e.g. to a new subject case).

For example, the characteristics, features or quantitative values of a new subject may be added to a databank of subject data, to which a clustering process according to an embodiment is applied. This will result in the new subject being grouped with similar existing or historical cases with a high degree of accuracy and good separation between the groups. This would allow a clinician to more accurately diagnose a new subject, as the subject is more likely to have a same diagnosis as subjects grouped therewith. Similarly, the improved grouping will also allow a clinician to observe historical treatment options (i.e. performed on similar subjects) and outcomes of those options. This allows a clinician to select a most appropriate option based on a known outcome for a similar subject (in a similar group). Overall, the proposed methods result in significantly improved subject outcome, as the outcomes, treatments and diagnoses of similar (historical) subjects may be exploited or utilized to improve subject outcome.

Figure 2:
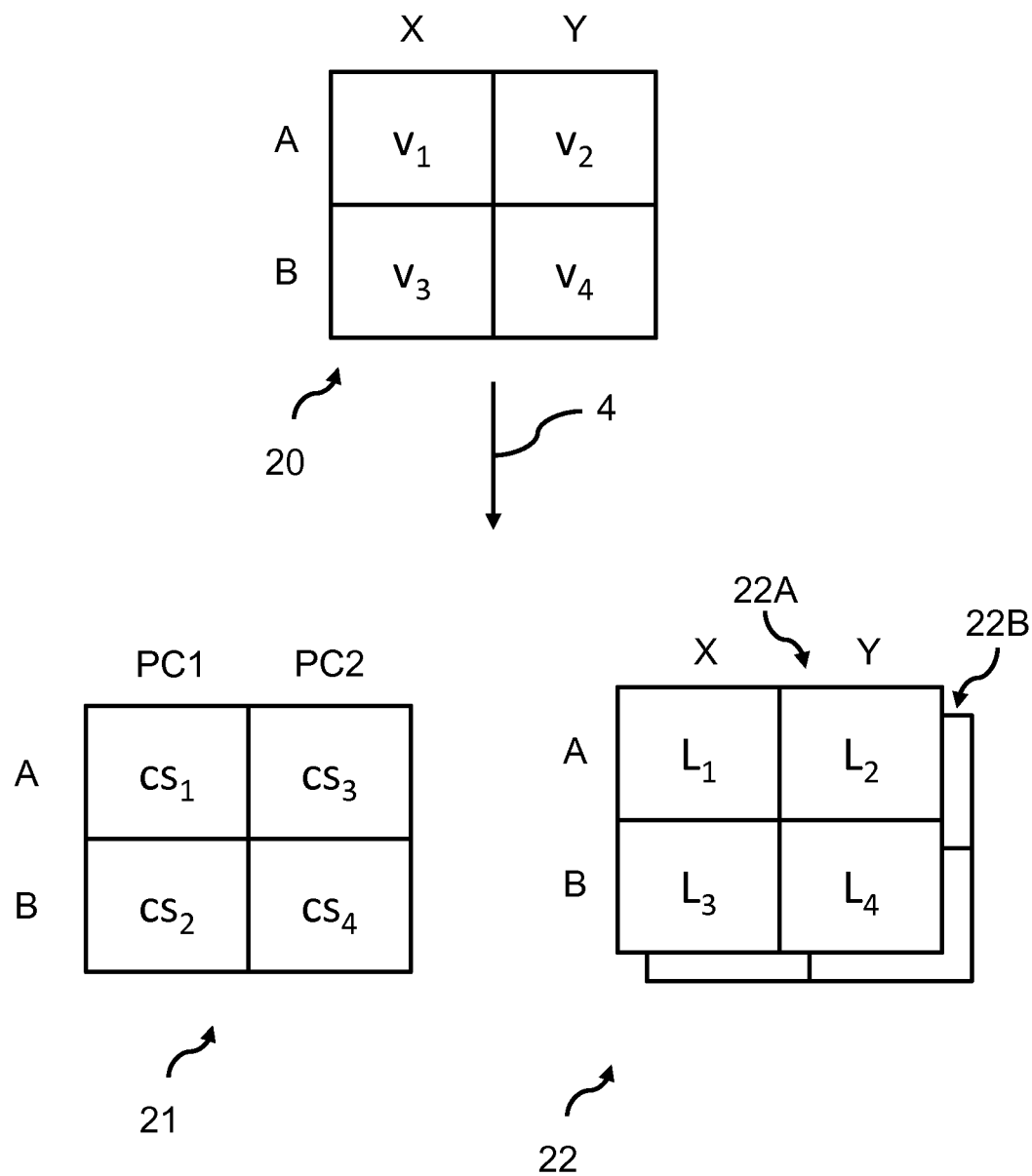
FIG. 2 shows a concept of performing a principal component analysis on a dataset of subject data.

Although PCA methods would be well known to the skilled person, for the sake of improved understanding in the context of the present invention, FIG. 2 illustrates a step 4 of performing a principal component analysis, PCA, on a (simplified) initial dataset 20 of subject data.

The dataset 20 of subject data comprises a first A set of quantitative values $v_1$, $v_2$ and a second B set of quantitative values $v_3$, $v_4$. Each set A, B is associated with a different subject, and can be considered to represent a record of that subject. Each quantitative value $v_1$, $v_2$ in a set A represents a different (clinical or pathological) feature or characteristic X, Y for that particular subject, and can thereby represent a field of a subject's record. For example, quantitative value $v_1$ represents a value for a characteristic X (e.g. a subject's age) of subject A and quantitative value $v_3$ represents a value for the same characteristic X of a different subject B.

Performing a PCA step 4 generates a dataset 21 of component scores, sometimes called factor scores, which identifies at least two principal components PC1, PC2. Each principal component PC1 is associated with a set of components scores $cs_1$, $cs_2$. Each component score $cs_1$, $cs_2$ of a principal component PC1 is associated with a respective set A, B of quantitative values, i.e. a respective subject. For example, a first component score $cs_1$ is associated with the first set A of quantitative values, whereas a second component score $cs_2$ is associated with the second set B of quantitative values. A component score is understood to be a transformed variable value which represents relative variance of the associated set of quantitative values of the subject data.

Performing the PCA step 4 also generates a plurality 22 of (loading) datasets 22A, 22B of loadings, sometimes called loading values. Each loading dataset 22A is associated with a different principal component PC1. For example, a first dataset 22A is associated with the first principal component PC1 and a second dataset 22B is associated with the second principal component PC2. Each dataset 22A comprises loadings $L_1$, $L_2$, $L_3$, and $L_4$. A loading $L_1$ represents a weight or value by which a standardized quantitative value $v_1$ should be multiplied to obtain a component score $cs_1$ associated with the set of quantitative values containing the quantitative value $v_1$. By way of example, a second loading $L_2$ is equal to the component score $cs_1$ divided by the standardized quantitative value $v_2$. Thus, each loading $L_1$ in a dataset 22A can be mapped to a respective quantitative value $v_1$.

A standardized quantitative value is a quantitative value which has been (statistically) standardized or normalized with respect to other quantitative values in the same set of quantitative values. Thus, a step 4 of performing a PCA may comprise a sub-step (not shown) of generating a standardized dataset of subject data.

By way of further explanation, it is noted that PCA is mathematically defined as an orthogonal linear transformation that transforms data to a new coordinate system such that the greatest variance by some projection of the data lies on the first coordinate (called the first principal component), the second greatest variance on the second coordinate (second principal component), and so on. This is explained in some detail in Jolliffe I. T. Principal Component Analysis, Series: Springer Series in Statistics, 2nd ed., Springer, N.Y., 2002, XXIX, 487 p. 28 illus. ISBN 978-0-387-95442-4.

Figure 3:
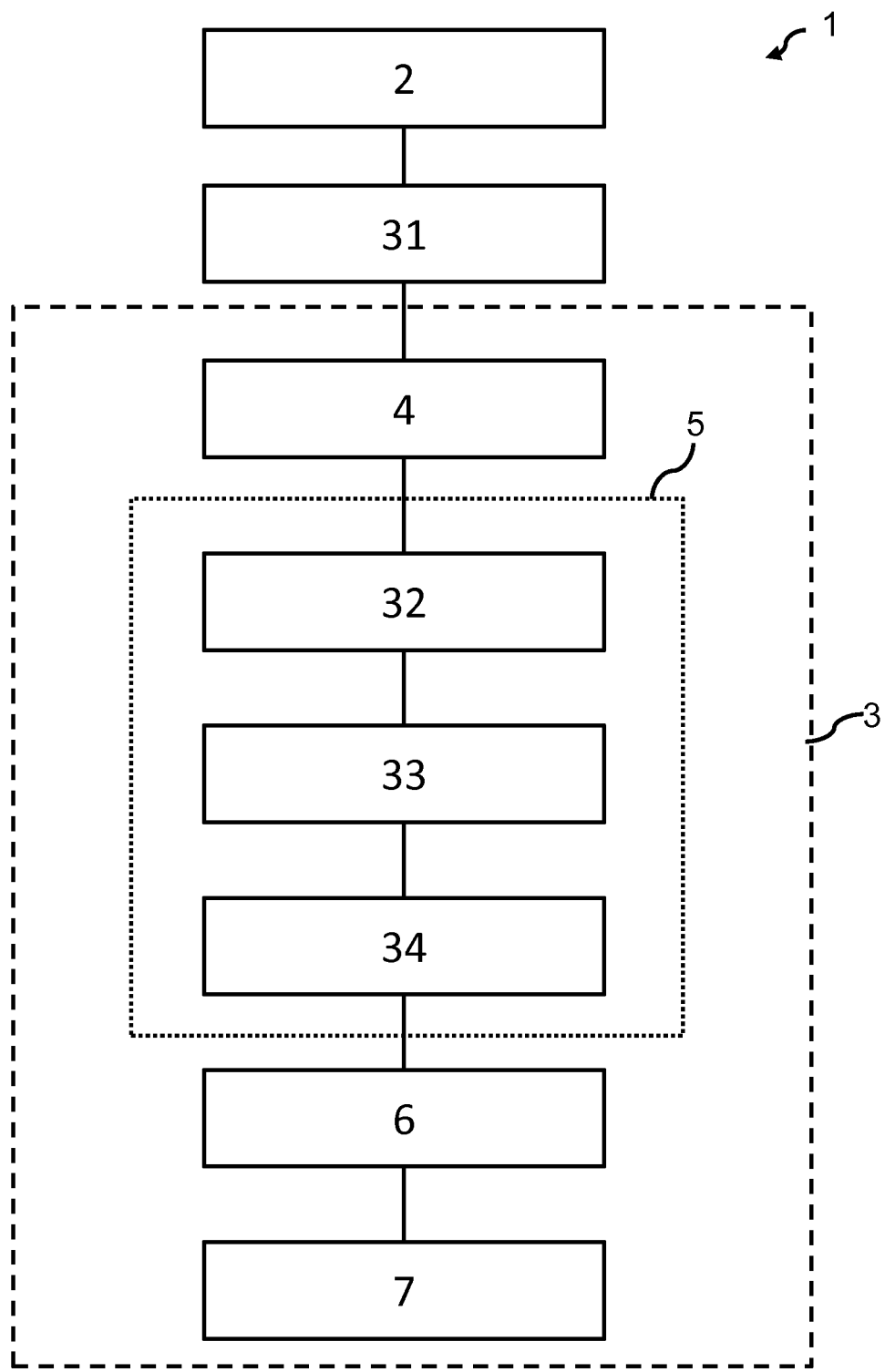
FIG. 3 illustrates a method of clustering subjects according to a second embodiment.

FIG. 3 illustrates a second embodiment of the method 1, being a modified version of the first embodiment.

The modified method 1 further comprises a step 31 of obtaining a second dataset of weighting values. The obtained second dataset may, for example, be a past or historical dataset of weighting values. By way of example, the obtained second dataset may have been generated in a previous iteration, as explained below, or may have been generated based on a different set of subject data. In other embodiments, the obtained second dataset is an initial dataset of arbitrary values, for example, wherein the weighting values are all initialized to 1 or are randomly (or pseudorandomly) selected numbers between 0 and 1.

The step 5 of generating the first dataset of weighting values comprises modifying the weighting values of the second dataset. In particular, the modifying the weighting values of the second data set is based upon the loading dataset of one of the two first principal components.

The step 5 may comprise a step 32 of selecting one of the first two principal components. Preferably, the step 32 comprises randomly or pseudorandomly selecting one of the first two principal components, but may instead comprise selecting only the first principal component or the second principal component. As would be appreciated by the person skilled in the art, the first two principal components are the two components generated by a PCA which explain most of the variance in the dataset of subject data.

The step 5 may further comprise a step 33 of multiplying each weighting value in the second dataset of weighting values by a respective loading in the dataset of loading values associated with the selected principal component. The number of weighting values in the second dataset of weighting values is equal to the number of loading values in the dataset of loading values. In this way, each weighting value is modified based on a respective loading in a loading dataset.

The step 5 may further comprise a step 34 of dividing each weighting value in the second dataset of weighting values by a randomly or pseudorandomly selected number between 0 and 1. Thus, the steps 33 and 34 together comprise multiplying each weighting value in the second dataset of weighting values by a proportion of a respective loading in the dataset of loading values.

The step 5, as described with reference to FIG. 3, of generating the first dataset of weighting values by modifying a second dataset of weighting values is particularly advantageous when used in an iterative procedure for calculating a suitable dataset of weighting values, such as those described later.

In particular, a randomness may be introduced into an iterative procedure by step 5, allowing for a heuristic search and/or a heuristic optimization approach. In particular, this randomness results in a fair diversification capability of a search procedure, which is preferably provided by a non-deterministic (i.e. random) selection between the most influential two principal components, and also by the random proportion of the loadings of the selected principal component.

The step 4 of performing the principal component analysis may be performed on the dataset of subject data weighted by the second dataset of weighting values.

Figure 4:
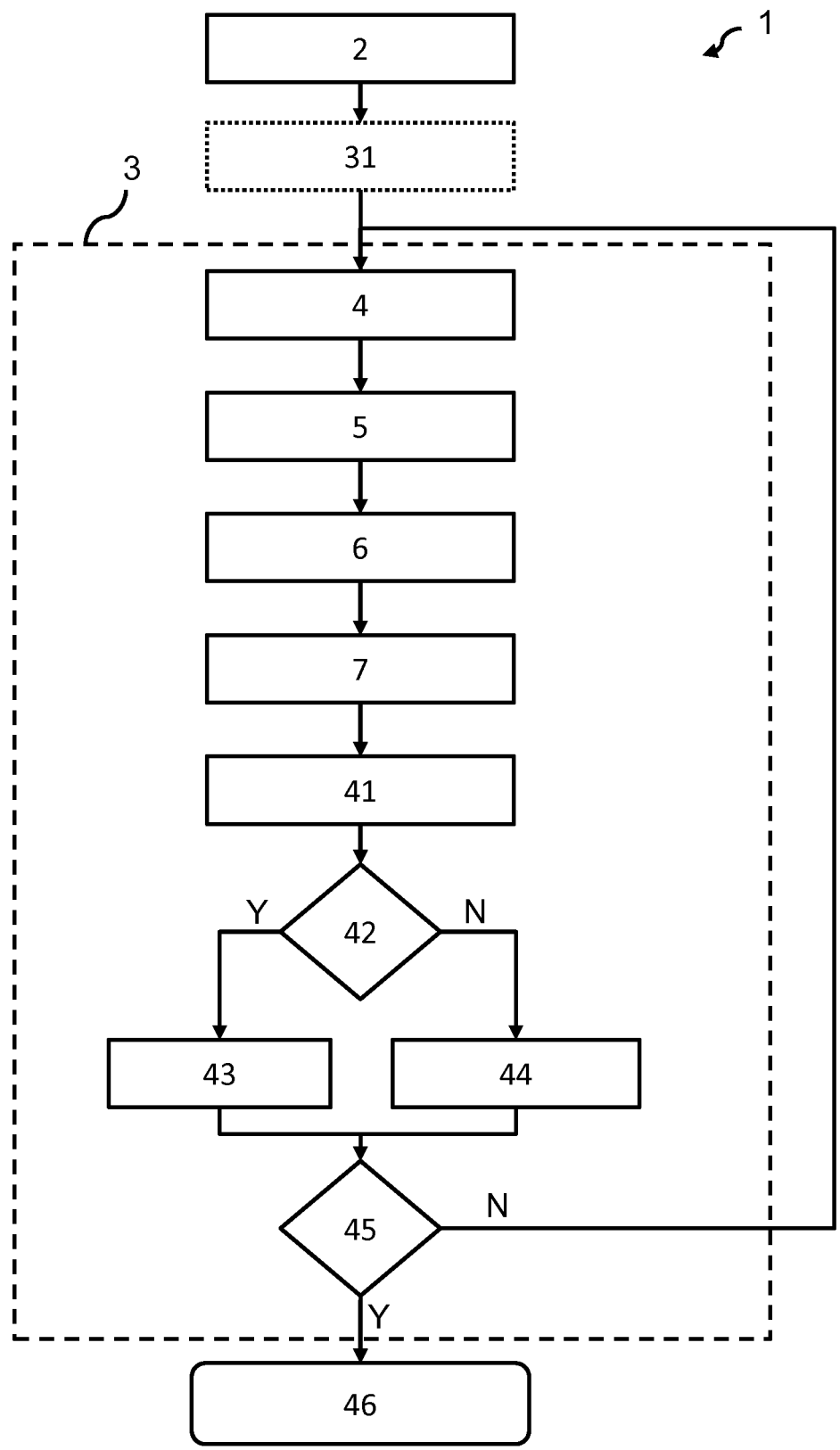
FIG. 4 illustrates a method of clustering subjects according to a third embodiment.

FIG. 4 illustrates a method 1 according to a third, modified embodiment.

In the third embodiment, the clustering process 3 is performed iteratively to optimize a dataset of weighting values (e.g. by determining whether the dataset of weighting values have converged in consecutive iterations).

In particular, iterative modifications may be made to a dataset of weighting values, where a determination is made (during each iteration) as to whether an improvement results from any modifications made. Non-improving modifications may be rejected, and improving modifications may be accepted. This advantageously allows for gradual convergence to the most suitable or otherwise optimized dataset of weighting values.

The method 1 comprises a step 41 of calculating a quality value of the clustering performed by the clustering algorithm (in step 7). Various methods of calculating a quality value would be readily anticipated by the skilled person, including calculating, for example, an average silhouette width, a Dunn index and a Davies-Bouldin index. A silhouette width can be calculated using any known distance metric, such as a Euclidean distance.

The method further comprises a step 42 of determining, whether the quality value is greater than a first predetermined threshold.

The method 1 comprises, in response to the quality value being greater than the predetermined threshold, a step 43 of replacing the weighting values of the second dataset of weighting values with the weighting values of the first dataset of weighting values.

Similarly, the method 1 comprises, in response to the quality value being less than the predetermined threshold, a step 44 of rejecting the weighting values of the first dataset of weighting values and retaining the weighting values of the second dataset of weighting values.

The first predetermined threshold is preferably the quality value of a clustering performed by the clustering algorithm on the dataset of subject data weighted using the second dataset of weighting values. In particular, the quality value may be the quality value calculated in a previous iteration of the clustering process 3. In this way, modifications which improve the dataset of weighting values are retained, and modifications which adversely affect the dataset of weighting values are rejected, discarded or otherwise disposed.

In some other embodiments, the first predetermined threshold is a proportion or fraction of the quality value of the previous iteration. Using a fraction of the previous quality value (e.g. 0.95 of the previous quality value) improves the diversification of the algorithm by exploring slightly worse solutions. This could lead to more promising regions of the solution search space being identified.

Similarly, in other embodiments, multiplies (e.g. >1×, such as 1.1×) of the quality value of the previous iteration may be also used as the first predetermined threshold. This may ensure that only solutions that are significantly better than a previous solution are identified, and may lead to more promising paths.

The first dataset of weighting values is a current dataset (i.e. of a current iteration), and the second dataset of waiting values is, e.g. for the second and subsequent iterations, a previous dataset (i.e. of a previous iteration) or, e.g. for a first iteration, an initialized or default dataset of weighting values as obtained in step 31.

The clustering process 3 thereby modifies or otherwise generates a new dataset of weighting values (e.g. based on a previous set) and determines whether the new dataset of weighting values advantageously or adversely effects the quality of a clustering performed on a dataset of subject data weighted by the weighting values. In examples, a quality value generated in a previous clustering process is compared to a quality value generated in a current clustering process. The previous clustering process is a clustering process performed on the dataset of subject data when weighted using a previous dataset of weighting values, i.e. the second dataset of weighting values. The current clustering process in a clustering process performed on the dataset of subject data when weighting using a newly generated dataset of weighting values, i.e. the first dataset of weighting values.

The clustering process 3 may further comprise a step 45 of determining whether to discontinue the iterative clustering process 3, to thereby determine whether to prevent further iterations of the clustering process 3 from being performed.

The step 45 may comprise determining whether the number of iterations is greater than the predetermined iteration number (e.g. around 25, or around 50), or determining whether a length of time elapsed during the iterative clustering process, being the time during which the clustering process 3 is repeated, is greater than a predetermined length of time (e.g. around one minute, around 10 minutes, or around 30 minutes). In either event, the step 45 determines to discontinue the iterative clustering process 3 when the measured value is above the respective predetermined value (e.g. when the number of iterations is greater than the predetermined iteration number).

The predetermined length of time may depend upon the size of the dataset, e.g. number of quantitative values in the dataset, number of sets and/or number of quantitative values in a set). Of course, the computational time may also depend upon the type of device performing the computations and/or availability of said device.

For smaller sets (e.g. <10,000 quantitative values), it has been identified that a generally acceptable computational running time is in the region of 1-30 minutes. In more complex cases (e.g. >10,000 quantitative values), a generally acceptable running time is in the region of 1-2 hours.

The predetermined iteration number may depend upon the size of the dataset (e.g. a number of sets of quantitative values and/or a number of quantitative values in a set). In one embodiment, the predetermined iteration number is no less than the total number of quantitative values in the dataset divided by 500, for example, no less than the total number of quantitative values in the dataset divided by 1000. These values have been identified as providing suitably accurate weighting values whilst minimizing computation time and thereby improving efficiency.

In some examples, the predetermined iteration number is no less than 50, for example, no less than 100. These values have shown to provide suitable and accurate identification of appropriate weights without excessive computation time or iteration.

Preferably, the step 45 instead comprises determining whether the quality value (calculated in step 41) is greater than a second predetermined threshold. The second predetermined threshold may depend upon the type of quality value calculated, by way of example only the second predetermined threshold may, when the quality value is an average silhouette width, be around 0.5, or 0.7.

Alternatively, the step 45 may comprise determining whether a number of consecutive rejections of the first dataset of weighting values is greater than a predetermined number of rejections. Such a method would identify whether the dataset of weighting values has converged with a high degree of confidence. The predetermined number of rejections made, for example be in the region of 10 or 15.

Other suitable determinations may be made, for example, determining whether a quality value (calculated in step 41) has remained substantially unchanged (e.g. ±1%) for a predetermined number of iterations. This may also indicate that a dataset of weighting values has converged towards an optimized dataset of weighting values.

Of course, the step 45 may combine any of the preceding determinations as alternatives for determining whether to stop performing the iterative process (e.g. the process 3 is stopped if a quality value is above a second predetermined threshold or a time elapsed is greater than a predetermined length of time).

The method may end at step 46 if it is determined to discontinue performing the iterative clustering process 3. In particular the iterative clustering process may be stopped when a measured value (quality value, number of iterations, amount of time performing iterations, number of rejections of first dataset of weighting values) is above a predefined threshold value. The predefined threshold value may be defined by a user or according to known principles described above.

At step 46, the weighted dataset of subject data (i.e. as weighted using the second dataset of weighting values) or the output of a clustering process, as performed in step 7, may be output, stored, displayed or otherwise provided to a user of the method.

In each iteration, the step 4 of performing the principal component analysis is performed on the database of subject data which has been weighted by the second dataset of weighting values. Thus, principal components (with component scores and sets of loadings) are identified for each iteratively weighted dataset of subject data. This ensures that the method may account for the most significant variance which remains after a weighting of the subject data, and thereby further allow for further optimization of the dataset of weighting values.

In an embodiment, the step 4 of performing PCA may thereby comprise weighting or modifying dataset of the subject data using the second dataset of weighting values, or may instead comprise using the weighting dataset of subject data generated in step 6 of a previous iteration. In some embodiments, the step 4 of performing PCA is not repeated in a subsequent iteration if it is determined in step 42 that the quality value (associated with a newly calculated dataset of weighting values) is less than a first predetermined threshold value, rather a stored PCA performed in a previous iteration may be used instead.

Figure 5:
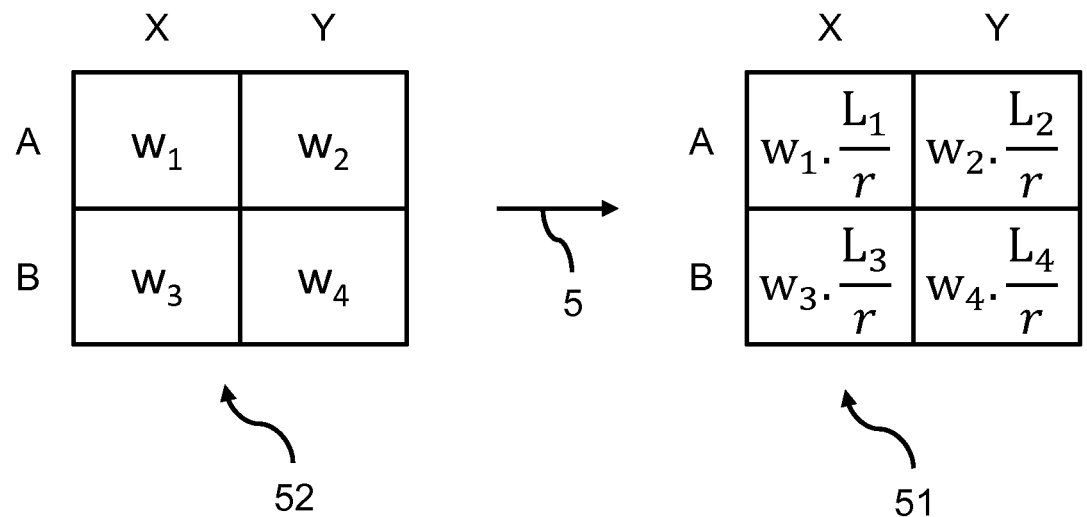
FIG. 5 shows a concept of generating a dataset of weighting values.

FIG. 5 illustrates a step 5 of generating the first dataset 51 of weighting values according to an embodiment.

The step 5 comprises modifying a second dataset 52 of weighting values $w_1$, $w_2$, $w_3$ and $w_4$. The second dataset 52 of weighting values may, for example, be a dataset of weighting values generated in a previous clustering process 3 iteration, or may be an initialized dataset of weighting values (e.g. all the weighting values are set to 1 or set to a random number between 0 and 1).

The step 5 comprises multiplying each weighting value $w_1$ by a respective loading $L_1$. The loadings are selected from a loading set 51 associated with one of the first two principal components resulting from a PCA of the (previously weighted) subject data, as previously described.

The principal component is randomly or pseudorandomly selected to thereby introduce some randomness to the weighting process. The step 5 may also comprise dividing each weighting value $w_1$ by a random or pseudorandom number between 0 and 1.

In an iterative process, introducing a randomness into generating a new weighting value improves a diversification capability of the iterative clustering process. This makes it more probable that an improved dataset of weighting values can be identified during the iterative process (i.e. a quality value can be improved).

Modifying each weighting value may thereby be performed by multiplying each weighting value by:

$$\frac{L_{i,x,j}}{r} \quad (1)$$

where i is 1 or 2 and indicates the principal component selected (among the first two most influential components), x represents the relevant set of quantitative values or subject, j indicates the related characteristic or quantitative value, and r ($\in [0,1]$) is a random (e.g. double or floating) number selected between 0 and 1.

Figure 6:
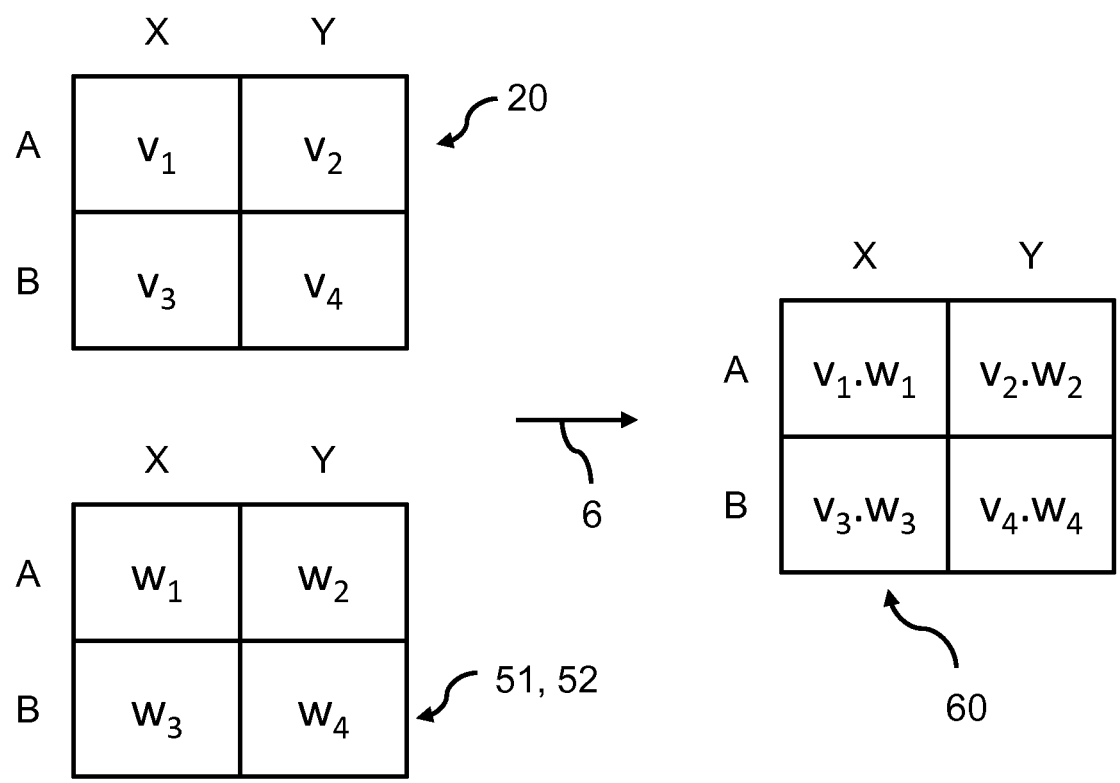
FIG. 6 shows a concept of modifying a dataset of subject values based on weighting values.

FIG. 6 illustrates a step 6 of weighting the quantitative values of the dataset 20 of subject data using a dataset 51, 52 of weighting values. This step may be performed at step 6 (before clustering subjects for determining a quality value) or during a principal component analysis step 5.

Each quantitative value of the dataset 20 can be mapped, associated or otherwise linked with a particular weighting. To weight the dataset, each quantitative value is multiplied by a respective weighting. By way of example, a first quantitative value $v_1$ may be multiplied by a first weighting value $w_1$. This results in a weighted dataset 60 of subject data.

Figure 7:
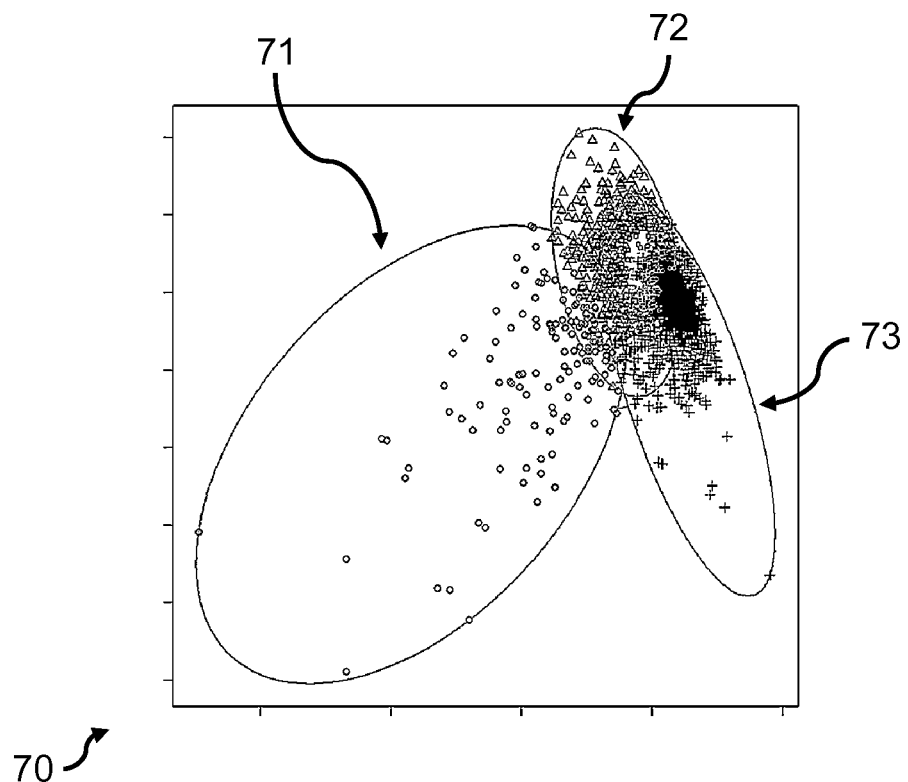
FIGS. 7 and 8 illustrate a result of performing a clustering algorithm on an unweighted dataset of subject values.
Figure 8:
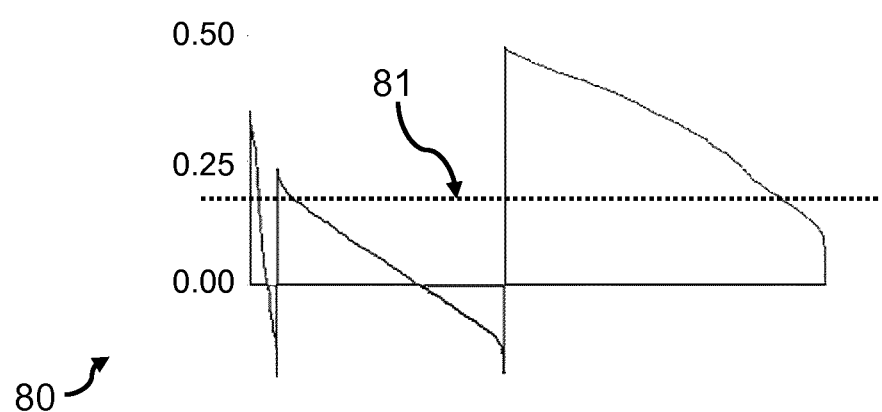
Figure 9:
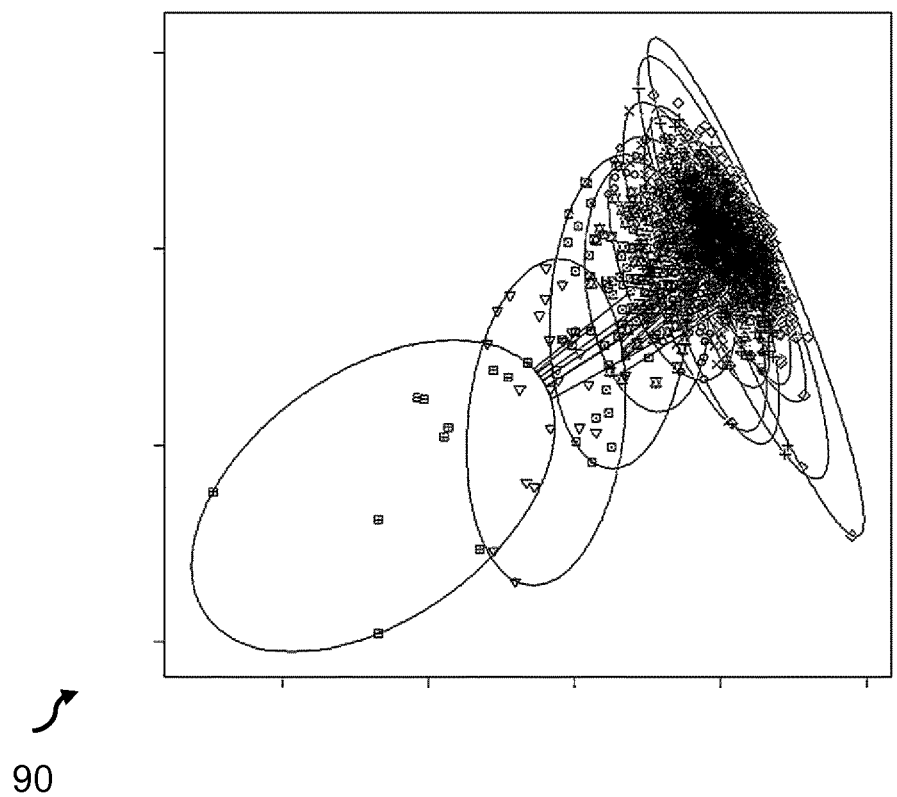
FIGS. 9 and 10 illustrate a result of performing a clustering algorithm on a weighted dataset of subject values according to an embodiment.
Figure 10:
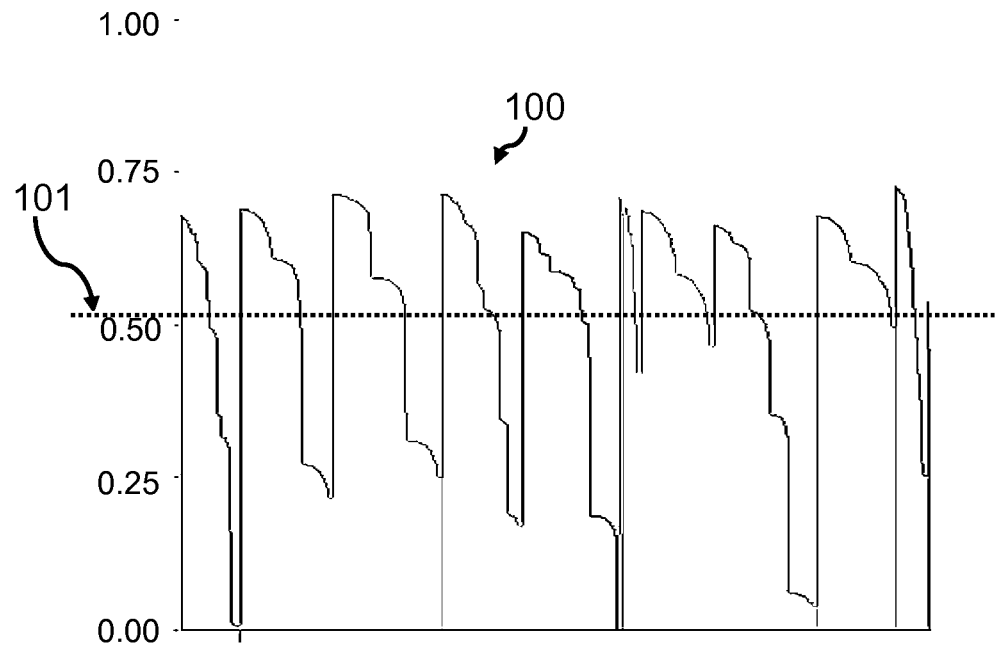

FIGS. 7, 8, 9 and 10 illustrate outcomes of clustering processes performed on an exemplary dataset of subject data in a real-life scenario, both without the use an iterative clustering process 3 (FIGS. 7 and 8) and with the use of an iterative clustering process 3 (FIGS. 9 and 10).

The exemplary dataset of subject data contains details of 2992 subjects at risk of prostate cancer tumors, all of whom underwent radical prostatectomy. The dataset contains, for each subject, a set of six quantitative values which respectively indicates the following clinical and pathology features of that subject: age at surgery, prostate specific antigen (PSA) density, percentage of positive biopsy cores, primary and second biopsy Gleason scores, and clinical stage.

When no (iterative) clustering process 3 is performed (i.e. the dataset of subject data is not weighted), a k-means clustering applied to the dataset of subject data results in a first Bivariate Clusters plot 70, also known as Clusplot, shown in FIG. 7. The Clusplot 70 graphically displays the subjects as points in a bivariate plot and graphically displays clusters of these subjects as ellipses of various sizes and shapes. Of course, information indicating the clusters of subjects may also be stored in a memory. When no iterative clustering process 3 is performed, the subjects are clustered into three distinct and separate groups 71, 72, 73.

A first clusters silhouette plot 80, shown in FIG. 8, is also generated. The clusters silhouette plot graphically represents a separation of the grounds 71, 72 and 73. An average silhouette width 81 or score may be calculated. Generally, a clustering is considered satisfactory if a silhouette width is above 0.5. As shown in FIG. 8, the average silhouette width 81 is much below this threshold, being around 0.2, which suggests a poor separation of data for the produced three clusters.

When an iterative clustering process 3 is performed, according to an embodiment previously described, a k-means clustering of the appropriately weighted subject data results in a second Bivariate Cluster Plot 90, shown in FIG. 9. In particular, the weighted dataset has been clustered into twelve groups of subjects.

A second clusters silhouette plot 100, shown in FIG. 10, illustrates how a quality of the clustering of the dataset has also been improved due to the optimized weighting of the dataset of subject data. In particular, the average Silhouette width 101 is equal to 0.51 (i.e. above the satisfactory value of 0.5).

The results produced by performing the described iterative method on a real-life dataset demonstrate the feasibility of the system and its capability of producing meaningful groups of similar subjects. The resulting groups of subjects are well-separated from one another, rather than being grouped in large agglomerations and/or being potentially misclassified. The subjects in each group are also spread within pairwise similarity boundaries, thereby ensuring placement of subjects that are radically different in different, well-separated groups.

In some embodiments, the clustering algorithm is performed on a result of a PCA analysis of the (weighted) subject data. In particular, the clustering may be performed to cluster subjects using the first two principal components (of the subject data) as determined by the PCA analysis. The clustering shown in FIGS. 7 through 10 have been clustered according to such a method. This may further improve a process of clustering and further improve a similarity between subjects in a same group.

In above-described and other embodiments, the subject data includes clinical and pathology features belonging to different domains, and having different variation ranges and statistical distributions. Each such feature, j, may be referred to as $F_j$. A generic subject i, may be referred to as: $P_i=[F_{i1}; F_{i2}; \ldots ; F_{ij}; \ldots F_{in}]$, where n is the total number of clinical or pathological features. The whole dataset of subject data may therefore be: $P=[F_1; F_2; \ldots ; F_j; \ldots F_n]$. The aim of the iterative clustering process is to find the dataset of weights, w, that improves subjects clustering to the greatest extent, thereby resulting in an optimized dataset of subject data: $P=[w_1.F_1; w_2.F_2; \ldots; w_j.F_j; \ldots w_n.F_n]=w.F$. This optimized dataset better represents the overall subject data, improving statistical similarity and reducing statistical variation and distribution within the dataset.

Initially, the weighting values may be set equal to one, i.e. $w'=[1; 1; \ldots 1]$, thereby forming the second dataset of weighting values obtained in step 31 previously described. A perturbation of these weighting values is performed, obtaining a new dataset of weighting values, w", and thereby forming the first dataset of weighting values. If the new dataset of weighting values w" leads to an improved weighted dataset, associated with an improved quality value or 'objective function value', then the perturbation to the dataset of weighting values is accepted and the new weighted dataset of subject values and new dataset of weighting values replace the previous respective datasets.

At each iteration, a quality of the clustering performed on the weighted subject data is assessed to obtain the quality value. The assessment may determine, for example, the average Silhouette width and/or the Dunn Index as the quality value.

Iterations of the optimization routine proceed until predefined stopping conditions are met. These may include, for example, any one or more of: a maximum allowed computation or CPU time, a maximum number of iterations, a maximum number of iterations between two improvements, or a minimum average silhouette width (e.g. at least 0.5), are satisfied. In this way, the integration of the multiple feature spaces (i.e. features of differing statistical characteristics) into a clustering algorithm is obtained.

In some embodiments, one or more of the quantitative values in the dataset may comprise NULL or missing values. This may occur if the dataset is missing some data (or data for particular subjects was not recorded). To overcome this issue, any missing values may be substituted by a default value (e.g. zero) or by providing an imputed or average value. Appropriate imputation methods will be well known to the skilled person. In other embodiments, sets of quantitative values comprising missing or NULL values are discarded.

Figure 11:
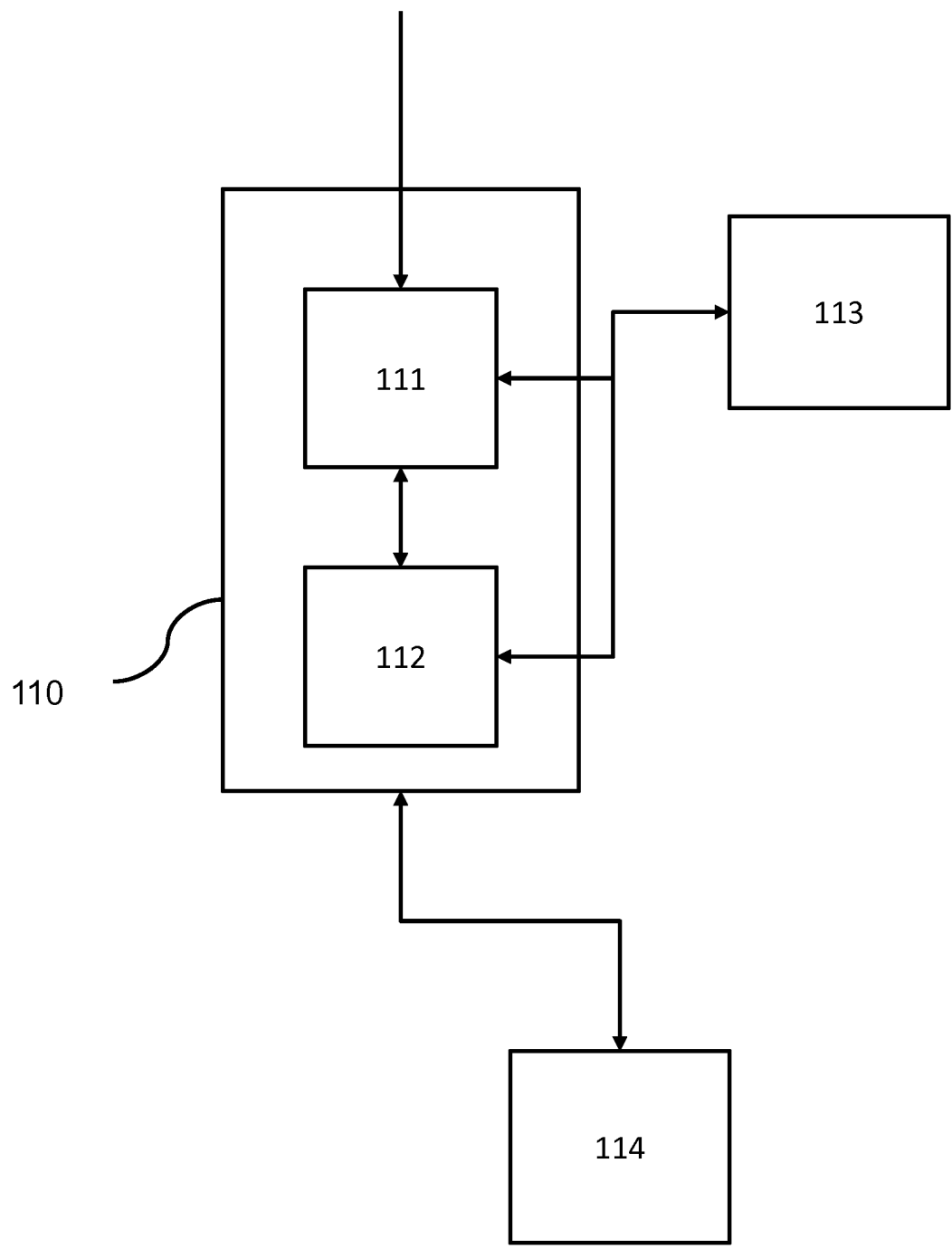
FIG. 11 illustrates a processor arrangement according to an embodiment.

FIG. 11 illustrates a processor arrangement 110 adapted to cluster similar subjects of a plurality of subjects, the processor arrangement comprising: an obtaining unit 111 and a clustering unit 112.

The obtaining unit 111 is adapted to obtain a dataset of subject data, the dataset containing a respective set of quantitative values for each subject, each quantitative value being a measurement of a clinical or pathological feature of the subject and each set of quantitative values having a same number of quantitative values.

The clustering unit 112 is adapted to perform a clustering process by: performing a principle component analysis on the dataset of subject data to identify at least two principle components, each principal component being associated with a component score and a dataset of loadings, the number of loadings in each dataset of loadings being equal to the number of quantitative values in a set of quantitative values; generating a first dataset of weighting values, the number of weighting values in the first dataset being equal to the number of loadings in a dataset of loadings, wherein each weighting value in the first dataset of weighting values is based on a respective loading in the dataset of loadings associated with one of the first two principal components; weighting the quantitative values using the first dataset of weighting values to obtain a weighted dataset of subject data; and performing a clustering algorithm on the weighted dataset of subject data so as to cluster similar subjects.

The obtaining unit 111 may obtain the dataset of subject data, for example, from an external source or from a memory arrangement 113. The clustering unit may be adapted to store the first dataset of weighting values and the weighted dataset of subject data in the memory arrangement 113.

Preferably, the obtaining unit 111 is adapted to obtain a second dataset of weighting values, the number of weighting values in the second dataset being equal to the number of quantitative values in the dataset of subject data. The second dataset of weighting data may be obtained from the memory arrangement 113, and may, for example, be a dataset of weighting values generated during a previous iteration (as previously described).

The clustering unit 111 may be adapted to generate the first dataset of weighting values by modifying each weighting value in the second dataset of weighting values based on a respective loading in the dataset of loadings associated with one of the first two principal components, to thereby obtain the first dataset of weighting values. The clustering unit 111 may store the first dataset of weighting values in the memory arrangement 113, which may be later obtained by the obtaining unit as the second dataset of weighting values for a subsequent iteration.

The clustering unit 111 may be adapted to iteratively perform the clustering process, wherein the clustering process further comprises: calculating a quality value indicative of the quality of the clustering performed by the clustering algorithm; in response to the quality value being greater than a first predetermined threshold, replacing the weighting values in the second dataset of weighting values with the weighting values in the first dataset of weighting values; and in response to the quality value being below the first predetermined threshold, rejecting the first dataset of weighting values and retaining the weighting values of the second dataset of weighting values.

Thus, the clustering unit 112 may only update a stored dataset of weighting values (in the memory arrangement 113) if a quality of a clustering algorithm has improved due to the modifications to the dataset of weighting values.

The processing arrangement 110 may communicate with a display device 114. In particular, the processing arrangement may display an outcome of a clustering process, a principal component analysis and so on. This may allow a user of the processing arrangement 110, such as a clinician, to readily access stored information.

Embodiments may make use of processor arrangement, such as a controller, to carry out any described method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

There may therefore be a computer program product comprising a computer readable storage medium having computer readable program instructions embodied therewith to, when executed on a processor arrangement, cause said processor arrangement to implement the method of any preceding method.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of clustering similar subjects of a plurality of subjects, the method comprising:
    obtaining a dataset of subject data, the dataset containing a respective set of quantitative values for each subject, each quantitative value being a measurement of a clinical or pathological feature of the subject and each set of quantitative values having a same number of quantitative values; and
    performing a clustering process comprising:
        performing a principal component analysis on the dataset of subject data to identify at least two principal components, each principal component being associated with component scores and a dataset of loadings, the number of loadings in each dataset of loadings being equal to the number of quantitative values in the dataset of subject data;
        generating a first dataset of weighting values, each weighting value being based on a respective loading in the dataset of loadings associated with one of the first two principal components, the number of weighting values in the first dataset being equal to the number of loadings in the dataset of loadings;
        weighting quantitative values of the dataset of subject data using the first dataset of weighting values to obtain a weighted dataset subject data; and
        performing a clustering algorithm on the weighted dataset of subject data so as to cluster similar subjects into groups of subjects having similar clinical characteristics, wherein subjects in each group of subjects have a similar diagnosis, predicted subject outcome and/or suitable treatment options.

2. The method of claim 1, further comprising a step of obtaining a second dataset of weighting values, the number of weighting values in the second dataset being equal to the number of quantitative values in the dataset of subject data, and
    wherein the step of generating the first dataset of weighting values comprises modifying each weighting value in the second dataset of weighting values based on a respective loading in the dataset of loadings associated with one of the first two principal components, to thereby obtain the first dataset of weighting values.

3. The method of claim 2, wherein the modifying each weighting value in the second dataset of weighting values comprises:
    selecting a dataset of loadings associated with one of the first or second principal components; and
    multiplying each weighting value in the second dataset of weighting values by a respective loading in the dataset of loadings associated with the selected principal component, to obtain a modified, first dataset of weighting values.

4. The method of claim 3, wherein the modifying each value in the second dataset of weighting values further comprises dividing each weighting value in the second dataset of weighting values by a randomly or pseudo-randomly selected number between 0 and 1.

5. The method of 2, wherein the modifying each value in the second dataset of weighting values comprises modifying each value in the second dataset of weighting values based on a respective loading in the dataset of loadings associated with a randomly or pseudorandomly selected one of the first two principal components.

6. The method of claim 2, wherein the performing the clustering process comprises iteratively performing the clustering process, and wherein the clustering process further comprises:
    calculating a quality value indicative of the quality of the clustering performed by the clustering algorithm;
    in response to the quality value being greater than a first predetermined threshold, replacing the weighting values in the second dataset of weighting values with the weighting values in the first dataset of weighting values; and
    in response to the quality value being below the first predetermined threshold, rejecting the first dataset of weighting values and retaining the weighting values of the second dataset of weighting values.

7. The method of claim 6, wherein the method comprises discontinuing performing the iterative clustering process in response to any one or more of:
    the quality value being greater than a second predetermined threshold;
    a number of iterations being greater than a predetermined iteration number;
    a length of time elapsed during the iterative clustering process being greater than a predetermined length of time; and
    a number of consecutive rejections of the first dataset of weighting values being greater than a predetermined number of rejections.

8. The method of claim 6, wherein the first predetermined value is a quality value of a clustering performed by the clustering algorithm based on the dataset of subject data weighted using the second dataset of weighting values.

9. The method of claim 8, further comprising, during the iterative clustering process and in response to the quality value being greater than a first predetermined threshold, replacing the first predetermined threshold with the quality value.

10. The method of claim 8, further comprising:
    weighting the quantitative values using the second dataset of weighting values to obtain an initial weighted dataset of subject data;

performing a clustering algorithm on the initial weighted dataset of subject data so as to cluster similar subjects; and calculating a quality value indicative of the quality of the clustering performed by the clustering algorithm to thereby obtain the first predetermined threshold.

11. The method of claim 6, wherein the calculating a quality value comprises calculating one or more of: a Dunn index; a Silhouette width and a Davies-Bouldin index.

12. A computer program product comprising a computer readable storage medium having computer readable program instructions embodied therewith to, when executed on a processor arrangement, cause said processor arrangement to implement the method of claim 1.

13. A processor arrangement adapted to cluster similar subjects of a plurality of subjects, the processor arrangement comprising:

an obtaining unit adapted to obtain a dataset of subject data, the dataset containing a respective set of quantitative values for each subject, each quantitative value being a measurement of a clinical or pathological feature of the subject and each set of quantitative values having a same number of quantitative values; and a clustering unit adapted to perform a clustering process by:
performing a principal component analysis on the dataset of subject data to identify at least two principal components, each principal component being associated with a component score and a dataset of loadings, the number of loadings in each dataset of loadings being equal to the number of quantitative values in a set of quantitative values;

generating a first dataset of weighting values, the number of weighting values in the first dataset being equal to the number of loadings in a dataset of loadings, wherein each weighting value in the first dataset of weighting values is based on a respective loading in the dataset of loadings associated with one of the first two principal components;

weighting the quantitative values using the first dataset of weighting values to obtain a weighted dataset of subject data; and performing a clustering algorithm on the weighted dataset of subject data so as to cluster similar subjects into groups of subjects having similar clinical characteristics, wherein subjects in each group of subjects have a similar diagnosis, predicted subject outcome and/or suitable treatment options.

14. The processor arrangement of claim 13, wherein:
the obtaining unit is adapted to obtain a second dataset of weighting values, the number of weighting values in the second dataset being equal to the number of quantitative values in the dataset of subject data, and the clustering unit is adapted to generate the first dataset of weighting values by modifying each weighting value in the second dataset of weighting values based on a respective loading in the dataset of loadings associated with one of the first two principal components, to thereby obtain the first dataset of weighting values.

15. The processor arrangement of claim 14, wherein the clustering unit is adapted to iteratively perform the clustering process, and wherein the clustering process further comprises:

calculating a quality value indicative of the quality of the clustering performed by the clustering algorithm;

in response to the quality value being greater than a first predetermined threshold, replacing the weighting values in the second dataset of weighting values with the weighting values in the first dataset of weighting values; and in response to the quality value being below the first predetermined threshold, rejecting the first dataset of weighting values and retaining the weighting values of the second dataset of weighting values.

16. A method, comprising:
determining a group corresponding to subject data for subject, wherein the group is one of the groups of subjects defined by the method of clustering in claim 1.

17. A computer program product comprising a computer readable storage medium having computer readable program instructions embodied therewith to, when executed on a processor arrangement, cause said processor arrangement to implement the method of claim 16.

18. A method, comprising:
receiving subject data for a subject;
performing the method of claim 1, wherein the subject data is included in the dataset; and
identifying a group in the groups of subjects that includes the subject data for the subject.

* * * * *